United States Patent [19]

Bodick et al.

[11] Patent Number: 5,574,028
[45] Date of Patent: Nov. 12, 1996

[54] METHOD FOR TREATING ANXIETY

[75] Inventors: Neil C. Bodick, Indianapolis; Franklin P. Bymaster, Brownsburg; Walter W. Offen, Indianapolis; Harlan E. Shannon, Carmel, all of Ind.

[73] Assignee: Eli Lilly and Company, Indianapolis, Ind.

[21] Appl. No.: 333,088

[22] Filed: Oct. 31, 1994

[51] Int. Cl.$^6$ ................................. A61K 31/395
[52] U.S. Cl. ........................................... 514/210
[58] Field of Search ............................. 514/210

[56] References Cited

U.S. PATENT DOCUMENTS

| | | | |
|---|---|---|---|
| 4,837,241 | 6/1989 | Jensen et al. | 514/340 |
| 4,873,331 | 10/1989 | Childers, Jr. et al. | 544/295 |
| 5,041,455 | 8/1991 | Sauerberg et al. | 514/342 |
| 5,043,343 | 8/1991 | Wyman | 514/299 |
| 5,043,345 | 8/1991 | Sauerberg et al. | 514/342 |
| 5,260,314 | 11/1993 | Sauerberg et al. | 514/305 |
| 5,328,923 | 7/1994 | Sauerberg et al. | 514/340 |
| 5,328,924 | 7/1994 | Sauerberg et al. | 514/340 |
| 5,484,794 | 1/1996 | Blodick et al. | 514/305 |

FOREIGN PATENT DOCUMENTS

WO95/05379-A1 2/1995 WIPO.
WO95/05174-A1 2/1995 WIPO.

OTHER PUBLICATIONS

Mathew, et al., *Am. J. Psychiatry.*, 137:9, 1118–1120, (1980).

Sim, M. and Houghton, H., *J. of Nervous and Mental Disease*, 143:6, 484–491, (1966).

Rapaport, et al., *Biol. Psychiatry*, 29, 658–664, (1991).

*Primary Examiner*—Marianne M. Cintins
*Assistant Examiner*—William R. A. Jarvis
*Attorney, Agent, or Firm*—Macharri R. Vorndran-Jones; David E. Boone

[57] ABSTRACT

The present invention provides a method for treating anxiety in a human in need thereof, comprising administering to the human an antianxiety amount of a muscarinic agonist compound of the general formula

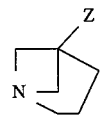

wherein Z is a 5-membered heterocyclic ring as defined in the disclosure.

1 Claim, No Drawings

METHOD FOR TREATING ANXIETY

BACKGROUND OF THE INVENTION

Extensive research has been conducted for a number of years directed toward the development of compounds capable of treating anxiety in humans that are safer to the user and which exhibit fewer side-effects. For example, several clinically established anxiolytic agents such as the barbituates, meprobamate and the benzodiazepines have numerous side effects such as potential for abuse and addiction or potentiation of the effects of ethanol. The mechanism of action of these compounds is believed to involve the GABA/benzodiazepine receptor complex in humans.

Buspirone is another compound which has been studied for the treatment of anxiety. The literature states that Buspirone interacts with reasonable potency only at the $5-HT_{1A}$ and dopamine receptors. Alfred Goodman, et al., *Goodman and Gilman's The Pharmacological Basis of Therapeutics*, 8:482 (1990); Tompkins et al. *Research Communications in Psychology, Psychiatry, and Behavior*, 5:4, p. 338 (1980).

The compounds employed in the present invention are known compounds taught to be compounds active at the muscarinic receptor.

As such, the compounds are taught to be useful in treating Alzheimer's disease, dementia, antispasmodics, urology, obstetrics, respiratory tract disorders, tardive dyskinesia, hyperkinesia, Tourette Syndrome, mania, severe painful conditions, and glaucoma. There is no disclosure or suggestion in the patents of using the compounds to treat anxiety.

The art has reported that compounds which act as agonists of the cholinergic muscarinic receptor can actually produce anxiety. See, Risch et al. *Psychopharmacol. Bull.*, 19: 696–698 (1983), Nurnberger et al. *Psychiatry Res.*, 9:191–200 (1983), and Nurnberger et al. *Psychopharmacol. Bull.* 17: 80–82 (1982).

Surprisingly, we have discovered that a group of compounds having muscarinic cholinergic activity can be useful for treating anxiety. The present invention relates to a method of treating anxiety. More specifically, the invention provides a method of treating anxiety in humans using specified compounds. The activity of these compounds is believed to be based on agonist action at the muscarinic cholinergic receptor.

As noted hereinbefore, the compounds employed in the method of the present invention are known. The compounds, method of preparing the compounds, as well as pharmaceutical formulations containing the compounds, are taught in U.S. Pat. Nos. 4,923,880, 5,110,828, 5,041,436, 5,278,170, 7,177,084, 4,992,436, 5,260,293, 4,996,201, 5,066,662, 5,066,665, 5,066,663, 4,988,688, 5,106,853, 5,192,765, 5,041,455, 5,043,345, 5,260,314, 5,310,911, 5,106,851, 5,068,237, 5,318,978, 5,242,927, 5,300,516, 5,089,505, 5,302,595, 5,219,871, 5,096,890, 5,164,386, 5,164,514, 5,157,160, 5,217,975, and 5,081,130 herein incorporated by reference.

SUMMARY OF THE INVENTION

The present invention provides a method for treating anxiety in humans comprising administering to a human in need thereof, an antianxiety dose of a compound selected from the group consisting of:

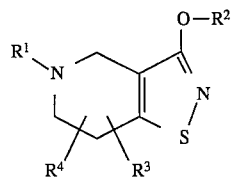

wherein $R^1$ is hydrogen, $C_1$–$C_6$ alkyl or phenyl-$C_1$–$C_4$ alkyl, in which the phenyl group may be substituted with halogen, $C_1$–$C_4$ alkyl or $C_1$–$C_4$ alkoxy;

$R^2$ is $C_1$–$C_6$ alkyl, $C_3$–$C_6$ alkynyl, branched or unbranched with 1–6 carbon atoms inclusive, which group may be optionally substituted with fluoro, hydroxy or phenyl optionally substituted with fluoro, trifluoromethyl, lower alkyl, hydroxy, or lower alkoxy;

$R^3$ and $R^4$ are independently hydrogen, $C_1$–$C_6$ alkyl, $C_3$–$C_6$ cycloalkyl, phenyl optionally substituted with halogen trifluromethyl, $C_1$–$C_4$ alkyl, hydroxy, or $C_1$–$C_4$ alkoxy, or phenyl-$C_1$–$C_4$ alkyl, in which the phenyl group may be substituted with halogen, $C_1$–$C_4$ alkyl or $C_1$–$C_4$ alkoxy;

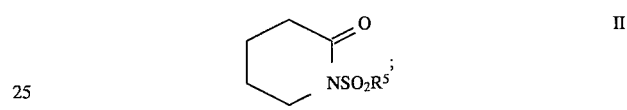

in which $R^5$ represents the radical

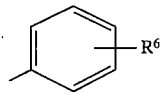

in which $R^6$ at any position on the benzene ring represents linear, branched or cyclic $C_1$–$C_8$ alkyl, $C_2$–$C_8$ alkenyl or $C_2$–$C_8$ alkynyl or the radical

in which $R^7$ and $R^8$ which may be identical or different represent hydrogen, linear $C_1$–$C_8$ alkyl, $C_2$–$C_8$ alkenyl or $C_2$–$C_8$ alkynyl or form together with the nitrogen atom to which they are attached a carbonaceous hetercyclic radical optionally containing another heteroatom, or the radical $OR^9$, $R^9$ representing hydrogen, linear, branched or cyclic $C_1$–$C_8$ alkyl, $C_2$–$C_8$ alkenyl or $C_2$–$C_8$ alkynyl or aryl containing up to 14 carbon atoms, or the radical $SR^{10}$ or $S(O)R^{11}$, $R^{10}$ and $R^{11}$ represent linear, branched or cyclic $C_1$–$C_8$ alkyl, $C_2$–$C_8$ alkenyl or $C_2$–$C_8$ alkynyl, or $R^5$ represents naphthyl optionally substituted with $R^{6'}$, $R^{6'}$ being defined above for $R^6$;

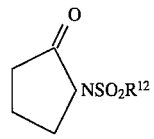

in which $R^{12}$ represents the radical

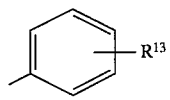

in which $R^{13}$ at any position on the benzene ring represents linear, branched or cyclic $C_1$–$C_8$ alkyl, $C_2$–$C_8$ alkenyl or $C_2$–$C_8$ alkynyl or the radical

in which $R^{14}$ and $R^{15}$ which may be identical or different represent hydrogen, linear $C_1$–$C_8$ alkyl, $C_2$–$C_8$ alkenyl or $C_2$–$C_8$ alkynyl or form together with the nitrogen atom to which they are attached a carbonaceous hetercyclic radical optionally containing another heteroatom, or the radical or $NO_2$, or $OR^{12'}$, $R^{12'}$ representing hydrogen, linear, branched or cyclic $C_1$–$C_8$ alkyl, $C_2$–$C_8$ alkenyl or $C_2$–$C_8$ alkynyl or aryl containing up to 14 carbon atoms, or the radical $SR^{16}$ or $S(O)R^{17}$, $R^{16}$ and $R^{17}$ represent linear, branched or cyclic $C_1$–$C_8$ alkyl, $C_2$–$C_8$ alkenyl or $C_2$–$C_8$ alkynyl, or $R^{12}$ represents naphthyl optionally substituted with $R^{13'}$, $R^{13'}$ being defined above for $R^{13}$;

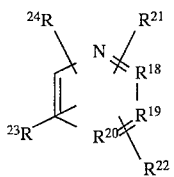

wherein, one of $R^{18}$, $R^{19}$, and $R^{20}$ represents nitrogen and the remainder represent carbon atoms; substituted on one of the ring carbon atoms with a $R^{24}$ substituent represented by a non-aromatic azacyclic or azabicyclic ring system and independently substituted on each of the other ring carbon atoms with $R^{23}$, $R^{21}$, or $R^{22}$ substituent of low lipophilicity or a hydrocarbon having a maximum of 20 carbon atoms;

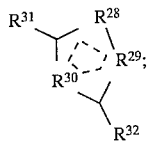

wherein one of $R^{28}$, $R^{29}$ or $R^{30}$ is an oxygen atom and the other two are nitrogen atoms, and the dotted circle represents aromaticity (two double bonds) thus forming a 1,3,4-oxadiazole or 1,2,4-oxadizole nucleus; $R^{31}$ represents a non-aromatic '927azacycle or '927azabicyclic ring system; and $R^{32}$ represents a substituent which is convertable in vivo to an amino group;

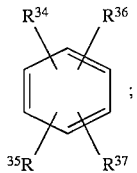

wherein $R^{34}$ represents a non-aromatic; non-fused 1-azabicyclic ring system; and $R^{35}$, $R^{36}$, and $R^{37}$ independently represent hydrogen, F, Cl, Br, —$CF_3$, —$OR^{38}$, —$NR^{38}R^{39}$, —$NHOR^{38}$, —$NHNH_2$, —CN, $COR^{40}$, or a substituted or unsubstituted, saturated or unsaturated hydrocarbon group, provided that at least one of $R^{35}$, $R^{36}$, and $R^{37}$ is other than hydrogen or a hydrocarbon group, or $R^{35}$ and $R^{36}$ or $R^{37}$ taken together form a $C_{1-6}$alkylenedioxy ring, wherein $R^{38}$ is $C_{1-6}$alkyl, $C_{2-6}$alkenyl or $C_{2-6}$alkynyl, $R^{39}$ is hydrogen, $C_{1-6}$alkyl, or —$COCH_3$, and $R^{40}$ represents OH, —$OR^{38}$, $NHR^{39}$, or —$NR^{38}R^{39}$

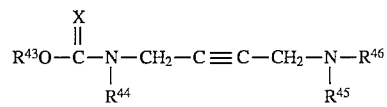

wherein
$R^{43}$ is
alkyl of from one to six carbon atoms,
alkyl of from one to six carbon atoms substituted with hydroxy or alkoxy of from one to four carbon atoms,
alkenyl of from two to six carbon atoms,
alkenyl of from two to six carbon atoms substituted with hydroxy or alkoxy of from one to four carbon atoms,
alkynyl of from two to six carbon atoms,
alkynyl of from two to six carbon atoms substituted with hydroxy or alkoxy of from one to four carbon atoms,
cycloalkyl of from three to six carbon atoms,

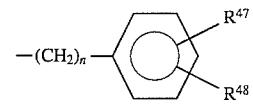

wherein n is zero or an integer of one to eight and
$R^{47}$ and $R^{48}$ are independently hydrogen, fluorine, chlorine, bromine, hydroxy, alkyl of from one to three carbon atoms, or alkoxy of from one to four carbon atoms, or

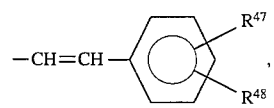

wherein
$R^{47}$ and $R^{48}$ are as defined above;
X is oxygen or sulfur;
$R^{44}$ is
alkyl of from one to six carbon atoms,
alkyl of from one to six carbon atoms substituted with hydroxy or alkoxy of from one to four carbon atoms,
alkenyl of from three to six carbon atoms
alkenyl of from three to six carbon atoms substituted with hydroxy or alkoxy of from one to four carbon atoms,
alkynyl of from three to six carbon atoms,
alkynyl of from three to six carbon atoms substituted with hydroxy or alkoxy of from one to four carbon atoms,
cycloalkyl of from three to six carbon atoms, or

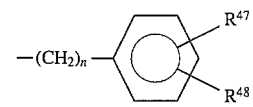

wherein n, $R^{47}$ and $R^{48}$ are as defined above;
$R^{45}$ and $R^{46}$ are each independently hydrogen,
alkyl of from one to twenty carbon atoms,
alkyl of from one to twenty carbon atoms substituted with hydroxy or alkoxy of from one to four carbon atoms,
alkenyl of from three to twenty carbon atoms,
alkenyl of from three to twenty carbon atoms substituted with hydroxy or alkoxy of from one to four carbon atoms,
alkynyl of from three to twenty carbon atoms, alkynyl of from three to twenty carbon atoms substituted with hydroxy or alkoxy of from one to four carbon atoms, cycloalkyl of from three to eight carbon atoms, phenyl, phenyl substituted with alkyl of from one to four carbon atoms, alkyl of from one to four carbon atoms substituted with hydroxy of alkoxy of from one to four carbon atoms, alkoxy of form one to four carbon atoms, chlorine, bromine, hydroxy, nitro or trifluoromethyl or $R^{45}$ and $R^{46}$ are taken together with the nitrogen atom to which they are attached to from a ring denoted by $$-N\begin{array}{c}CH_2\\ \\ CH_2\end{array}\bigg\langle\begin{array}{c}(CH_2)_n\\ \\ R^{49}\end{array}$$

wherein $R^{49}$ is hydrogen, alkyl of from one to ten carbon atoms, alkyl of from one to ten carbon atoms substituted with hydroxy or alkoxy of from one to four carbon atoms, alkenyl of from two to ten carbon atoms, alkenyl of from two to ten carbon atoms substituted with hydroxy or alkoxy of from one to four carbon atoms, alkynyl of from two to ten carbon atoms or alkynyl of from two to ten carbon atoms substituted with hydroxy or alkoxy of from one to four carbon atoms and n is as defined above, $$-N\diagup\hspace{-0.5em}\diagdown X$$

wherein X is as defined above or $$-N\diagup\hspace{-0.5em}\diagdown N-R^{50}$$

wherein $R^{50}$ is hydrogen or alkyl of from one to six carbon atoms,

VIII wherein $R^{51}$ is selected from the group consisting of

-continued $R^{52}$ is hydrogen, alkyl of from one to ten carbon atoms, alkynyl of from two to ten carbon atoms or aryl; n' is zero or an integer of one or two; X' is carbon or nitrogen; and ... represents a single or double bond with the proviso that when, --- represent a double bond X' is nitrogen and when --- represents a single bond X' is $CH_2$;

IX wherein $R^{53}$ is selected from the group consisting $R^{54}$, $R^{55}$, $R^{56}$, and $R^{57}$ are each independently hydrogen, alkyl of from one to ten carbon atoms, alkynyl of from two to ten carbon atoms, phenyl or phenyl substituted by one to four substituents selected from C1–C10alkyl, alkoxy, C1–C10halogen or trifluoromethyl; n" is an integer of one to two;

X wherein X is oxygen, sulfur, or $-N-R^{62}$ wherein $R^{62}$ is hydrogen or alkyl of from one to ten carbon atoms; $R^{58}$ is selected from the group consisting of

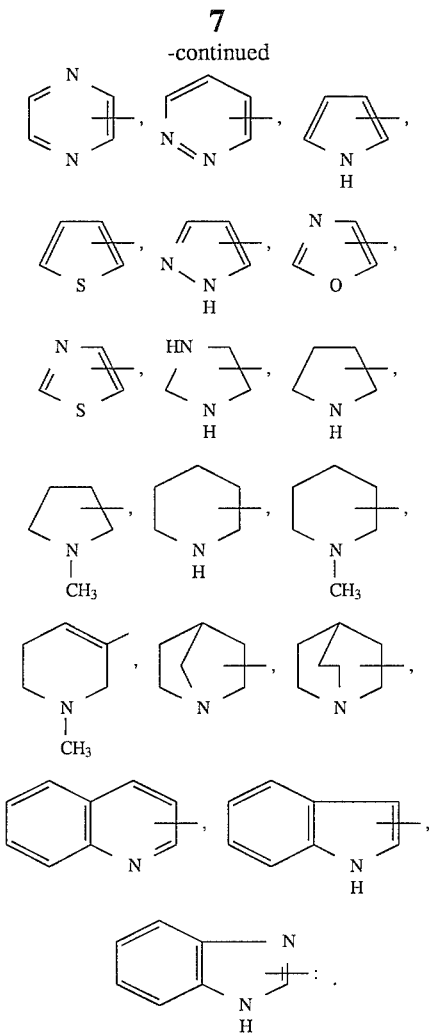

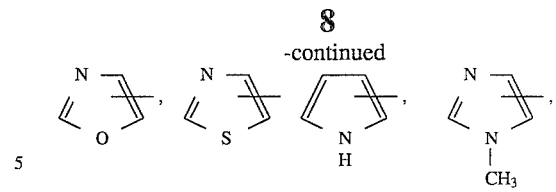

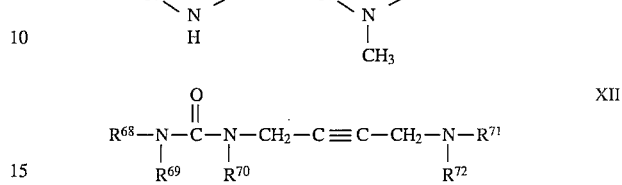

$R^{57}$, $R^{60}$, and $R^{61}$ are each independently hydrogen, alkyl of from one to ten carbon atoms, alkynyl of from two to ten carbon atoms or aryl; - - - represents a single or double bond with the proviso that when - - - represents a double bond $R^{59}$ and $R^{60}$ are absent;

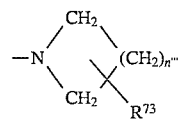    XI wherein $R^{63}$, $R^{64}$, and $R^{65}$ are each independently hydrogen, alkyl of from one to ten carbon atoms, alkynyl of from two to ten carbon atoms, phenyl or phenyl substituted by one to four substituents selected from the group consisting of alkyl, alkoxy, thioalkoxy, halogen, and trifluoromethyl; $R^{66}$ is hydrogen, hydroxy or alkoxy of from one to ten carbon atoms; and $R^{67}$ is selected from the group consisting of

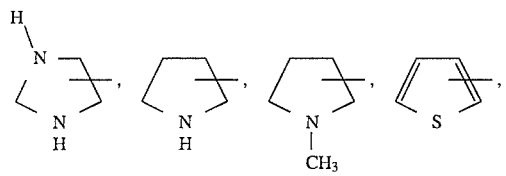

$$R^{68}-\underset{\underset{R^{69}}{|}}{N}-\overset{\overset{O}{\|}}{C}-\underset{\underset{R^{70}}{|}}{N}-CH_2-C\equiv C-CH_2-\underset{\underset{R^{72}}{|}}{N}-R^{71}$$    XII wherein $R^{68}$ is hydrogen and $R^{69}$ is hydrogen, alkyl of from one to six carbon atoms, alkyl of from one to six carbon atoms substituted with hydroxy of alkoxy of from one to four carbon atoms, alkenyl of from three to six carbon atoms, alkenyl of from three to six carbon atoms substituted with hydroxy or alkoxy of from one to four carbon atoms, alkynyl of from three to six carbon atoms, alkynyl of from three to six carbon atoms substituted with hydroxy of alkoxy of from one to four carbon atoms, cycloalkyl of from three to six carbon atoms, or $R^{68}$ and $R^{69}$ are taken together with the nitrogen atom to which they are attached to form a ring denoted by

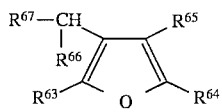

wherein $n^{81}$ is zero or an integer from one to eight and $R^{73}$ is hydrogen, alkyl of from one to ten carbon atoms, alkyl of from one to ten carbon atoms substituted with hydroxy or alkoxy of from one to four carbon atoms, alkenyl of from two to ten carbon atoms, alkenyl of from two to ten carbon atoms substituted with hydroxy or alkoxy of from one to four carbon atoms, alkynyl of from two to ten carbon atoms or alkynyl of from two to ten carbon atoms substituted with hydroxy or alkoxy of from one to four carbon atoms;

$R^{70}$ is hydrogen, alkyl of from one to six carbon atoms, alkyl of from one to six carbon atoms substituted with hydroxy or alkoxy of from one to four carbon atoms, alkenyl of from three to six carbon atoms, alkenyl of from three to six carbon atoms substituted with hydroxy or alkoxy of from one to four carbon atoms, alkynyl of from three to six carbon atoms, alkynyl of from three to six carbon atoms substituted with hydroxy of alkoxy of from one to four carbon atoms, cycloalkyl of from three to six carbon atoms, or $R^{70}$ when taken together with $R^{68}$ forms a ring denoted by

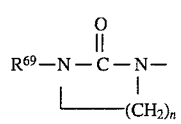

wherein n is an integer from one to three and $R^{68}$ are as defined above;

$R^{71}$ and $R^{72}$ are each independently hydrogen, alkyl of from one to twenty carbon atoms, alkyl of from one to twenty carbon atoms substituted with hydroxy or alkoxy of from one to four carbon atoms, alkenyl of from three to twenty carbon atoms, alkenyl of from three to twenty carbon atoms substituted with hydroxy or alkoxy of from one to four carbon atoms, alkenyl of from three to twenty carbon atoms, alkynyl of from three to twenty carbon atoms substituted with hydroxy or alkoxy of from one to four carbon atoms, cycloalkyl of from three to eight carbon atoms, phenyl, phenyl substituted with alkyl of from one to four carbon atoms, alkyl of from one to four carbon atoms substituted with hydroxy or alkoxy of from one to four carbon atoms, alkoxy of from one to four carbon atoms, chlorine, bromine, hydroxy, nitro or trifluoromethyl or $R^3$ and $R^4$ are taken together with the nitrogen atom to which they are attached to from a ring denoted by

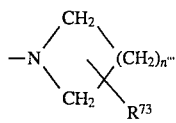

wherein n''' and $R^{78}$ are as defined above,

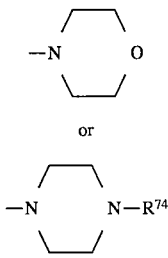

wherein $R^{74}$ is hydrogen or alkyl of from one to six carbon atoms,

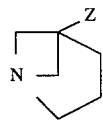 XIII in which Z is a heterocyclic group

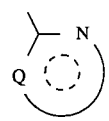

in which Q represents a 3-membered divalent residue completing a 5-membered aromatic ring and comprises one to two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or a group

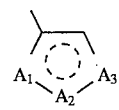

in which $A_1$, $A_2$ and $A_3$ complete a 5-membered aromatic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$ and $R_3$ are independently selected from hydrogen, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, cyclopropyl, $C_{2-5}$ straight chain alkenyl, $C_{2-5}$ straight chain alkynyl or $C_{1-5}$ straight chain alkyl optionally terminally substituted with $OR_4$, $N(R_4)_2$, $SR_4$, $CO_2R_4$, $CON(R_4)_2$ is one, two or three halogen atoms, in which each $R_4$ is independently hydrogen or $C_{1-3}$ alkyl and $R_5$ is $OR_4$, $NH_2$ or $NHR_4$; or in which Z is a group $—C(R_7)=NR_6$ in which $R_6$ is a group $OR_8$, where $R_8$ is $C_{1-4}$ alkyl, $C_{2-4}$ alkenyl, $C_{2-4}$ alkynyl, a group $OCOR_9$ where $R_9$ is hydrogen or $R_8$, or a group $NHR_{10}$ or $NR_{11}R_{12}$ where $R_{10}R_{11}$ and $R_{12}$ are independently $C_{1-2}$ alkyl and $R_7$ is hydrogen or $C_{1-4}$ alkyl, subject to the proviso that when $R_6$ is a group $OCOR_9$ or $NHR_{10}$, $R_7$ is $C_{1-4}$ alkyl;

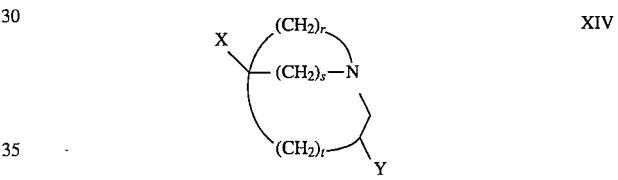 XIV in which one of X and Y represents hydrogen and the other represents Z', where Z' is a group

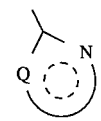

in which Q' represents a 3-membered divalent residue completing a 5-membered aromatic ring and comprises two to three nitrogen atoms, any amino nitrogen being substituted by a $C_{1-2}$ alkyl, cyclopropyl or propargyl group, r represents the integer of 2 or 3, s represents an integer of 1 or 2 and t represents 0, with the proviso that when Y is hydrogen s is 1;

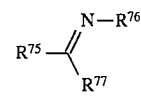 XV wherein $R^{75}$ represents

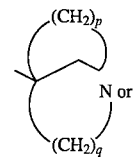

-continued

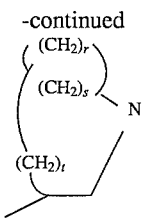

in which
each of p and q independently represents an integer of 2 to 4, r represents an integer of 2 to 4, s represents 1 or 2 and t represents 0 and 1;
$R^{76}$ is a group $OR^{78}$, where $R^{78}$ is $C_{1-4}$ alkyl, $C_{2-4}$ alkenyl, $C_{2-4}$ alkynyl, a group $OCOR^{79}$ where $R^{79}$ is hydrogen or $R^{78}$, or a group $NHR^{80}$ or $NR^{81}, R^{82}$ where $R^{80} R^{81}$ and $R^{82}$ are independently $C_{1-2}$ alkyl; and $R^{77}$ is hydrogen or $C_{1-4}$ alkyl, subject to the proviso that when $R^{76}$ is a group $OCOR^{79}$ or a group $NHR^{80}$, $R^{77}$ is alkyl;
(3R,4R)-3-(3-cyclopropyl-1,2,4-oxadiazol-5-yl)-1-azabicyclo[2.2.1heptane; or
a pharmaceutically acceptable salt or solvate thereof.

DETAILED DESCRIPTION

It is to be understood that the invention extends to the use of each of the stereoisomeric forms of the compounds of the present invention as well as the pure diastereomeric, pure enantiomeric, and racemic forms of the named compounds.

The term "low lipophilicity" refers to hydrogen, halogen, $-CR_3$, $-OR^{25}$, $-NR^{25}R^{26}$, $-NHOR^{25}$, $-NHNH_2$, $-CN$, $COR^8$, or a substituted or unsubstituted, saturated or unsaturated hydrocarbon group; wherein $R^{25}$ is hydrogen, $C_1-C_6$ alkyl, $C_{2-6}$ alkenyl or $C_{2-6}$ alkynyl; $R^{26}$ is hydrogen, alkyl or $-COCH_3$, and R27 represents $-OR^{25}$ or $-NR^{25}R^{26}$;

The term azacyclic or azabicyclic ring system is a non-aromatic ring system containing one nitrogen atom as the sole heteroatom. Suitably, the ring system contains from 4–10 ring atoms, preferably from 5–8 ring atoms. Preferably, the ring system contains a tertiary amino nitrogen atom in a caged structure. The bicyclic systems may be fused, spiro, or bridged. Preferably, the nitrogen atom is at a bridgehead in a bicyclic system. Examples of such heteroatoms include the heteroatoms described in U.S. Pat. No. 5,260,293, columns 2–3, which has been incorporated by reference.

The term "'927 azacyclic or '927 azabicyclic" refers to a non-aromatic ring system containing one nitrogen atom as the sole heteroatom. Suitably the ring contains from 4 to 10 ring atoms. Preferably from 5–8 ring atoms. The bicyclic systems may be fused, spiro or bridged. Examples of such heteroatoms include the bicyclic heteroatoms described in U.S. Pat. No. 5,242,927 column 2, which has been incorporated by reference. The most preferred '927azabicyclic or '927azacyclic systems include pyrrolidine, 1,2,5,6-tetrahydropyridine, quinuclidine or 1-azabicyclo[2.2.1]heptane ring, optionally substituted with methyl or hydroxy. An especially preferred '927 azabicyclic ring is quinuclidine, which is substituted by hydrogen, methyl or hydroxy at any available atom.

Groups which are converted in vivo to an amino group on the compounds claimed herein for treating anxiety may be ascertained by administering the compound to a human or an animal and detecting, by conventional analytical techniques, the presence of the corresponding compound having an amino substituent in the urine of a human or animal.

Examples of such groups include groups which are hydrolysable in vivo to an amino group, such as amido, urethan substituents. In particular a group of the formula $-NH.Q$ wherein Q represents CHO, $COR^{33}$ or $CO_2R^{33}$, and $R^{33}$ represents an optionally substituted hyrocarbon group. The term hydrocarbon group includes groups having up to 20 carbon atoms, suitably up to 10, and conveniently up to 8 carbon atoms. Suitable hydrocarbon groups include $C_{1-8}$ alkyl, $C_{2-8}$ alkenyl, $C_{2-8}$ alkynyl, $C_{3-7}$ cycloalkyl, $C_{3-7}$ cycloalkyl$C_{1-6}$ alkyl, aryl and aryl$C_{1-6}$ alkyl.

Suitable $R^{34}$ groups include the following:

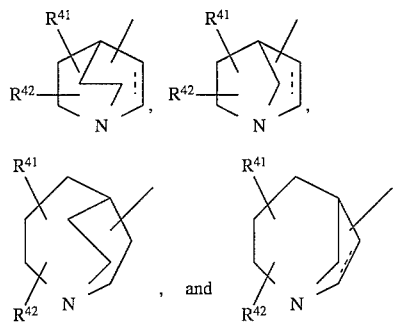

wherein the broken line represents an optional chemical bond; and $R^{41}$ and $R^{42}$ may be present at any position, including the point of attachment to the benzene ring, and independently represent hydrogen, $C_{1-4}$, F, Br, Cl, $C_{1-4}$ alkoxy, hydroxy, carboxy, or $C_{1-4}$ alkyoxycarbonyl or $R^{41}$ and $R^{42}$ together represent cabonyl. The nitrogen atom may be substituted by hydrogen or $C_{1-4}$ alkyl.

The term "phenyl-$C_1$-$C_4$ alkyl" designates an alkyl group which is substituted with a phenyl group. Preferred phenyl-alkyl groups include benzyl, 1- and 2-phenylethyl, 1-, 2-, 3-phenyla propyl and 1-methyl-1-phenylethyl. The phenyl group may be optionally be substituted with from 1–3 independently selected named substituents.

The term "form together with the nitrogen atom to which they are joined, a heterocyclic radical" means that a heterocyclic radical optionally containing another heteroatom, for example, S or O. Such groups include, but are not limited to, piperidyl, piperazynyl, morpholinyl, and pyrrolidinyl.

The term "alkyl" refers to the number of carbon atoms indicated; however, when no number is specified, the term refers to $C_{1-6}$ alky. The alkyl may be linear or branched unless specified.

The term "halogen" refers to chloro, bromo, and fluoro substituents.

The term "alkynyl" has its accepted means; however, if the number of carbon atoms are unspecified, it refers to $C_{2-10}$ alkynyl. The alkynyl group may be linear or branched unless specified.

The term alkoxy refers to $C_{1-4}$ alkoxy unless specified.

The term "antianxiety dose", as used herein, represents an amount of compound necessary to prevent or treat a human susceptible to or suffering from anxiety following administration to such human. The active compounds are effective over a wide dosage range. For example, dosages per day will normally fall within the range of about 0.005 to about 500 mg/kg of body weight. In the treatment of adult humans, the range of about 0.05 to about 100 mg/kg, in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way. While the present compounds are preferably administered orally to humans susceptible to or suffering from anxiety, the compounds may also be administered by a variety of other routes such as the transdermal, parenterally, subcutaneous, intranasal, intramuscular and intravenous routes. Such formulations may be designed to provide delayed or controlled release using formulation techniques which are known in the art.

As used herein the term "treating" includes prophylaxis of a physical and/or mental condition or amelioration or elimination of the developed physical and/or mental condition once it has been established or alleviation of the characteristic symptoms of such condition.

As used herein the term "anxiety" refers to an anxiety disorder. Examples of anxiety disorders which may preferredly be treated using an effective amount of a named compound or pharmaceutically acceptable salt thereof include, but are not limited to: Panic Attack; Agoraphobia; Acute Stress Disorder; Specific Phobia; Panic Disorder; Psychoactive Substance Anxiety Disorder; Organic Anxiety Disorder; Obsessive-Compulsive Anxiety Disorder; Posttraumatic Stress Disorder; Generalized Anxiety Disorder; and Anxiety Disorder NOS.

Examples of anxiety disorders which may more preferredly be treated using an effective amount of a named compound or a pharmaceutically acceptable salt thereof include Panic Attack; Panic Disorder; Psychoactive Substance Anxiety Disorder; Organic Anxiety Disorder; Obsessive-Compulsive Anxiety Disorder; Posttraumatic Stress Disorder; Generalized Anxiety Disorder; and Anxiety Disorder NOS.

Examples of the anxiety disorders which are most preferredly treated using a named compound include Organic Anxiety Disorder; Obsessive-Compulsive Disorder; Posttraumatic Stress Disorder; Generalized Anxiety Disorder; and Anxiety Disorder NOS.

The named anxiety disorders have been characterized in the DSM-IV-R. *Diagnostic and Statistical Manual of Mental Disorders,* Revised, 4Ed. (1994). The DSM-IV-R was prepared by the Task Force on Nomenclature and Statistics of the American Psychiatric Association, and provides clear descriptions of diagnostic categories. The skilled artisan will recognize that there are alternative nomenclatures, nosologies, and classification systems for pathologic psychological conditions and that these systems evolve with medical scientific progress.

The compounds employed in the invention are not believed to act via the GABA/benzodiazepine, 5HT1A, or D1 receptor systems in humans. Rather, the activity of the present compounds as antianxiety agents is believed to be based upon modulation of muscarinic cholinergic receptors. However, the mechanism by which the present compounds function is not necessarily the mechanism stated supra., and the present invention is not limited by any mode of operation.

The following Examples are studies to establish the usefulness of the named compounds for treating anxiety.

EXAMPLE 1

Punished Responding

The antianxiety activity of the compounds employed in the method of the present invention is established by demonstrating that the compounds increase punished responding. This procedure has been used to establish antianxiety activity in clinically established compounds.

According to this procedure, the responding of rats or pigeons is maintained by a multiple schedule of food presentation. In one component of the schedule, responding produces food pellet presentation only. In a second component, responding produces both food pellet presentation and is also punished by presentation of a brief electric shock. Each component of the multiple schedule is approximately 4 minutes in duration, and the shock duration is approximately 0.3 seconds. The shock intensity is adjusted for each individual animal so that the rate of punished responding is approximately 15 to 30% of the rate in the unpunished component of the multiple schedule. Sessions are conducted each weekday and are approximately 60 min in duration. Vehicle or a dose of compound are administered 30 min in duration. Vehicle or a dose of compound are administered 30 min to 6 hr before the tart of the test session by the subcutaneous or oral route. Compound effects for each dose for each animal are calculated as a percent of the vehicle control data for that animal. The data are expressed as the mean ± the standard error of the mean.

EXAMPLE 2

Monkey Taming Model

Further, the antianxiety activity of the compounds is established by demonstrating that the compounds are effective in the monkey taming model. Plotnikoff *Res. Comm. Chem. Path. & Pharmacol.,* 5: 128–134 (1973) described the response of rhesus monkeys to pole prodding as a method of evaluating the antiaggressive activity of a test compound. In this method, the antiaggressive activity of a compound was considered to be indicative of its antianxiety activity. Hypoactivity and ataxia were considered to be indicative of a sedative component of the compound. The present study is designed to measure the pole prod response-inhibition induced by a compound of this invention in comparison with that of a standard antianxiety compound such as diazepam as a measure of antiaggressive potential, and to obtain an indication of the duration of action of the compound.

Male and female rhesus or cynomologous monkeys, selected for their aggressiveness toward a pole, are housed individually in a primate colony room. Compounds or appropriate vehicle are administered orally or subcutaneously and the animals are observed by a trained observer at varying times after drug administration. A minimum of three days (usually a week or more) elapses between treatments. Treatments are assigned in random fashion except that no monkey receives the same compound two times consecutively.

Aggressiveness and motor impairment are graded by response to a pole being introduced into the cage as described in Table 1. The individuals responsible for grading the responses are unaware of the dose levels received by the monkeys.

TABLE 1

Grading of Monkey Response to Pole Introduction

| Response | Grade | Description |
|---|---|---|
| Attack | 2 | Monkey immediately grabbed and/or bit pole as it was placed at opening in cage. |
| | 1 | Monkey grabbed and/or bit pole only after the tip was extended into the cage 12 inches or more. |
| | 0 | No grabbing or biting observed. |
| Pole Push | 2 | Monkey grabbed the pole to attack it or push it away. |
| | 1 | Monkey touched the pole only in attempting to avoid it or rode on the pole (avoidance). |
| | 0 | No pushing, grabbing or riding of the pole observed. |
| Biting | 2 | Monkey bit aggressively and frequently. |
| | 1 | Monkey bit weakly or infrequently |
| | 0 | No biting observed. |
| Ataxia | 2 | Monkey exhibited a marked loss of coordination. |
| | 1 | Slight loss of coordination observed. |
| | 0 | No effects on coordination observed. |
| Hypoactivity | 2 | Marked: Monkey was observed in a prone position. May or may not have responded by rising and moving away when experimenter approached. |
| | 1 | Slight: Monkey did not retreat as readily when experimenter approached |
| | 0 | None. |
| Antiaggression Activity of Drug Dose | + | Dose of drug was active in decreasing global assessment of aggressive behavior |
| | − | Dose of drug was not active in decreasing aggresive behavior |

EXAMPLE 3

Human Clinical Trials

Finally, the antianxiety activity of the named compounds can be demonstrated by human clinical trials. The study was designed as a double-blind, parallel, placebo-controlled multicenter trial. The patients were randomized into four groups, placebo and 25, 50, and 75 mg tid of test compound. The dosages were administered orally with food. Patients were observed at four visits to provide baseline measurements. Visits 5–33 served as the treatment phase for the study.

During the visits, patients and their caregivers were questioned and observed for signs of agitation, mood swings, vocal outbursts, suspiciousness, and fearfulness. Each of these behaviors are indicative of the effect of the test compound on an anxiety disorder.

For example, one test compound produced the following results:

| Behavioral Event | p | Placebo (N = 87) n (%) | 25 mg (N = 85) n (%) | 50 mg (N = 83) n (%) | 75 mg (N = 87) n (%) |
|---|---|---|---|---|---|
| Agitation | .006 | 40 (46) | 34 (40) | 24 (29) | 20 (23) |
| Mood swings | .025 | 40 (46) | 25 (29) | 21 (25) | 28 (32) |
| Vocal Outbursts | .001 | 33 (38) | 29 (34) | 24 (29) | 11 (13) |
| Suspiciousness | .001 | 32 (37) | 23 (27) | 26 (31) | 7 (8) |
| Fearfulness | .038 | 25 (29) | 28 (33) | 19 (23) | 13 (15) |

Treatment groups were compared with respect to the number and percent of patients who ever had the symptom during the double-blind portion of the study (visits 5 through 33), at a severity that was worse than during the baseline visits (1 through 4).

Preferred compounds for use in treating anxiety include:

(3R, 4R)-3-(3-cyclopropyl-1,2,4-oxadiazol-5-yl)-1-azabicyclo[2.2.1heptane and compounds of Formulae IV, V, VIII, IX, XIII, XIV, and XV; or a pharmaceutically acceptable salt thereof.

Especially preferred compounds include the following: compounds of Formulae XIII, XIV, and XV.

Examples of preferred compounds include, but are not limited to, 3-[2-(6-hydroxypyrazin)yl]-1-azabicyclo[2.2.2.]octane, 3-(2-pyrazinyl)-1-azabicyclo[2.2.1]heptane, 6-(2-pyrazinyl)-1-azabicyclo[3.2.1]octane, 6-(2-pyrazinyl)-1-azabicyclo[3.2.1]octan-6-ol, 3-fluoro-3-(2-pyrazinyl)-1-azabicyclo[2.2.1]heptane, 1-methyl-3-(2-pyrazinyl)pyrrolidine, 3-[2-(3-methylpyrazin)yl]-1-azabicyclo[2.2.2]octan-3-ol, 3-[2-(3,6-dimethylpyrazin)yl]-1-azabicyclo[2.2.1]heptane, 3-[2-(6-allyloxypyrazin)yl]-1-azabicyclo[2.2.2]octane, 3-[2-(6-chloropyrazin)yl]-1,2,5,6-tetrahydropyridine, 3-[5-(3-octanyloxycarbonylamino-1,2,4-oxadiazol)-yl]-1-azabicyclo[2.2.1]heptane, 3-[5-(3-cyclohexylcarbonylamino-1,2,3-oxadiazol)-yl]quinuclidine, 3-[5-(3-(1-(3-n-pentyloxycarbonyl)-1-ethoxycarbonylamino)-1,2,4-oxadiazol)-yl]quinuclidine, 3-(5-(3-octanoylamino-1,2,4-oxadiazol)-yl]quinuclidine, 3-[(1-methyl-1H-imidazol-5-yl()methyl]1,2,4-oxadiazol-5(4H)-one, 4-methyl-3-[(1-methyl-1H-imidazol-4-yl)-methyl]1,2,4-oxadizol-5(4H)-one, 4-ethyl-3[(1-methyl-1H-imidazol-4-yl)-methyl]-1,2,4-oxadiazol-5(4H)-one, N-[4-(hexahydro-1H-azaepin-1-yl)-2-butynyl]-N,N-dimethyl urea, N-[4-1-pyrrolidinyl)-2-butynyl]-urea, 5-acetyl-1-azabicyclo [3.1.1]heptane, 1-azabicyclo[3.1.1]hept-5-ylcarboxaldehyde, 3-(2-methyltetrazol-5-yl)-1-azabicyclo[2.2.1]heptane, 3-(2-methyl-1,2,3-triazol-4yl)-1-azabicyclo-[2.2.2]octane, 3-(3-cyclopropyl-1,2,4-oxadiazol-5-yl)-1-azabicyclo[2.2.1]heptane, and a pharmaceutically acceptable salt or solvate thereof.

We claim:

1. A method for treating anxiety in a human in need thereof, comprising administering to said human an antianxiety amount of a compound of the formula:

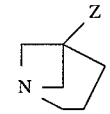

in which Z is a heterocyclic group

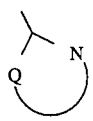

in which Q represents a 3-membered divalent residue completing a 5-membered aromatic ring and comprises one or two heteroatoms selected from oxygen, nitrogen and sulphur, or three nitrogen atoms, any amino nitrogen being substituted by a $C_{1-2}$ alkyl, cyclopropyl or propargyl group, and any ring carbon atom being optionally substituted by a group $R_1$; or Z is a group

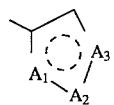

in which $A_1$, $A_2$ and $A_3$ complete a 5-membered aromatic ring and $A_1$ is oxygen or sulphur, one of $A_2$ and $A_3$ is $CR_2$, and the other is nitrogen or $CR_3$; or $A_2$ is oxygen or sulphur, one of $A_1$ and $A_3$ is $CR_2$ and the other is $CR_3$; and $R_1$, $R_2$ and $R_3$ are independently selected from hydrogen, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, cyclopropyl, $C_{2-5}$ straight chain alkenyl, $C_{2-5}$ straight chain alkynyl or $C_{1-5}$ straight chain alkyl optionally terminally substituted with $OR_4$, $N(R_4)_2$, $SR_4$, $CO_2R_4$, $CON(R_4)_2$ or one, two or three halogen atoms; each $R_4$ is independently hydrogen or $C_{1-3}$ alkyl;

$R_5$ is $OR_4$, $NH_2$ or $NHR_4$; or z is a group $-C(R_7)=NR_6$;

$R_6$ is a group $OR_8$;

$R_7$ is hydrogen or $C_{1-4}$ alkyl;

$R_8$ is $C_{1-4}$ alkyl, $C_{2-4}$ alkenyl, $C_{2-4}$ alkynyl, or $-OCOR_9$;

$R_9$ is hydrogen, $R_8$, or a group $NHR_{10}$ or $NR_{11}R_{12}$;

$R_{10}$, $R_{11}$ and $R_{12}$ are independently $C_{1-2}$ alkyl; subject to the proviso that, when $R_6$ is $OCOR_9$ or $NHR_{10}$, $R_7$ is $C_{1-4}$ alkyl;

or a pharmaceutically acceptable salt or solvate thereof.

* * * * *